(12) United States Patent
Sanchez et al.

(10) Patent No.: US 8,003,550 B2
(45) Date of Patent: Aug. 23, 2011

(54) METHOD FOR REVEALING EMERGENT DISLOCATIONS IN A GERMANIUM-BASE CRYSTALLINE ELEMENT

(75) Inventors: Loic Sanchez, La Murette (FR); Chrystel Deguet, Saint Ismier (FR)

(73) Assignee: Commissariat à l'Energie Atomique, Paris (FR)

( * ) Notice: Subject to any disclaimer, the term of this patent is extended or adjusted under 35 U.S.C. 154(b) by 0 days.

(21) Appl. No.: 12/654,441

(22) Filed: Dec. 18, 2009

(65) Prior Publication Data
US 2010/0184303 A1 Jul. 22, 2010

(30) Foreign Application Priority Data
Jan. 16, 2009 (FR) ..................................... 09 00198

(51) Int. Cl.
*H01L 21/30* (2006.01)
(52) U.S. Cl. ................................ 438/795; 257/E21.111
(58) Field of Classification Search .................. 438/795; 257/E21.211
See application file for complete search history.

(56) References Cited

U.S. PATENT DOCUMENTS

| 6,403,385 | B1 | 6/2002 | Venkatkrishnan et al. | |
| 7,531,427 | B2 * | 5/2009 | Daval | 438/455 |
| 2007/0254440 | A1 * | 11/2007 | Daval | 438/285 |
| 2009/0309118 | A1 * | 12/2009 | Song | 257/99 |

FOREIGN PATENT DOCUMENTS

| EP | 1 758 158 A2 | 2/2007 |
| WO | WO 2005/086222 A1 | 9/2005 |

OTHER PUBLICATIONS

Souriau, L., et al; "A Wet Technique to Reveal Threading Dislocations in Thin Germanium Layers," Solid State Phenomena Scitec Publications Ltd. Switzerland, Jan. 1, 2008, vol. 134, No. xp0081009913, pp. 83-86.
French Search Report for French Patent Application No. 09 00198 dated Aug. 17,2009 (w/ Eng. Translation).

* cited by examiner

*Primary Examiner* — Alexander G Ghyka
*Assistant Examiner* — Stanetta D Isaac
(74) *Attorney, Agent, or Firm* — Oliff & Berridge, PLC

(57) ABSTRACT

The invention relates to a method for detecting defects, more particularly emergent dislocations of an element having at least one crystalline germanium-base superficial layer. The method comprises an annealing step of the element in an atmosphere having a base that is a mixture of at least an oxidizing gas and a neutral gas enabling selective oxidizing of the emergent dislocations of the crystalline germanium-base superficial layer.

13 Claims, 3 Drawing Sheets

METHOD FOR REVEALING EMERGENT DISLOCATIONS IN A GERMANIUM-BASE CRYSTALLINE ELEMENT

BACKGROUND OF THE INVENTION

The invention relates to a method for revealing emergent dislocations of an element having at least one crystalline germanium-base superficial layer.

STATE OF THE ART

The electrical properties of a material are influenced by the presence of defects in the crystal lattice of the semi-conductor material. More particularly, the emergent dislocations that pass through the upper layers of the material give indications on the quality of the semi-conducting properties of the material. Several dislocation revelation and evaluation techniques exist, in particular for emergent dislocations. Transmission electron microscopy (TEM) or X-ray topography techniques enable crystal lattice defects to be detected as a whole. It is difficult to distinguish between emergent dislocations and buried dislocations, i.e. dislocations that are not propagated to the surface. Buried dislocations do not however have any influence on the electrical properties of the useful superficial film. Interpretation of the results obtained is consequently difficult to perform.

Other commonly used techniques consist in revealing surface defects by chemical wet process or vapor deposition etching. The surface of the sample can be previously oxidized and then subjected to an etching solution, generally hydrochloric or hydrofluoric acid, which selectively etches the oxide thus formed. The etching rate of the areas presenting dislocations is greater than that of the perfect single crystal. Segregation is then performed revealing the dislocations preferentially. The dislocations are revealed by segregation and then appear in the form of recessed points directly observable for example under an optical or electronic microscope.

In the article "A Wet Etching Technique to Reveal Threading Dislocations In Thin Germanium Layers" (Solid State Phenomena, vol. 134 (2008), 83-86), Souriau et al. describe for example a method for revealing dislocations by wet etching of thin germanium layers. Revelation of the dislocations is achieved by immersing germanium wafers in etching solutions with chromium and hydrofluoric acid.

The document WO2005/086222 further describes a method for revealing emergent dislocations by chemical vapor deposition etching of a silicon-base and/or germanium-base single crystal film at the surface of a substrate. More particularly, the etching gas is gaseous hydrofluoric or hydrochloric acid. In addition to requiring handling of gaseous products that are corrosive and harmful for man and the environment, the disclosed method is implemented in a complex and costly epitaxy installation.

OBJECT OF THE INVENTION

The object of the invention is to propose a method for revealing emergent dislocations of an element having at least one crystalline germanium-base superficial layer remedying the shortcomings of the prior art.

In particular, the object of the invention is to propose a method that is simple to implement, inexpensive and efficient for both germanium bulk substrates and for germanium thin layers and in particular layers with a thickness of less than 500 nm.

According to the invention, this object is achieved by a method for revealing emergent dislocations according to the appended claims. In particular, this object is achieved by the fact that it comprises an annealing step of the element in an atmosphere having a base that is a mixture of at least an oxidizing gas and a neutral gas.

According to a particular embodiment, the oxidizing gas is oxygen and the neutral gas is nitrogen and/or argon. The proportion of oxygen in the mixture is comprised between 0.5% and 95%.

BRIEF DESCRIPTION OF THE DRAWINGS

Other advantages and features will become more clearly apparent from the following description of particular embodiments of the invention given as non-restrictive examples only and represented in the appended drawings, in which.

DESCRIPTION OF PARTICULAR EMBODIMENTS OF THE INVENTION

Figure 1:
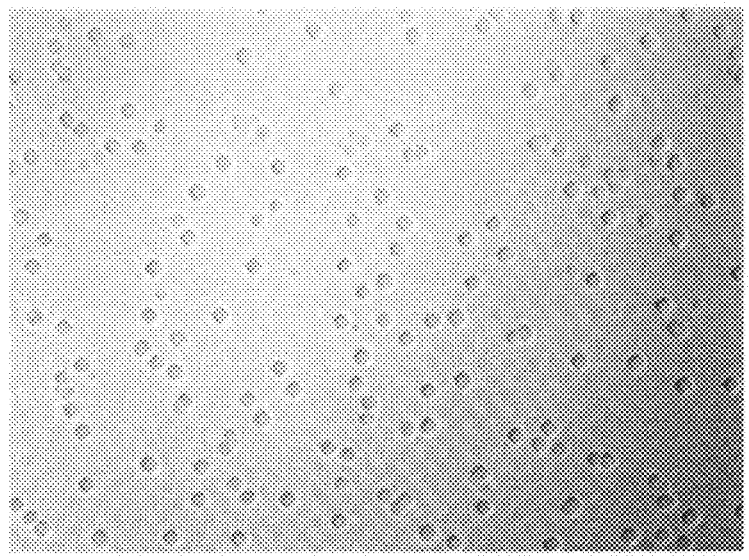
FIG. 1 represents an optical micrograph of a sample of a first GOS (1) wafer after revelation according to the method of the invention.

The invention relates to a method for detecting defects, more particularly for detecting emergent dislocations of an element having at least one crystalline germanium-base superficial layer. Germanium is a semi-conducting element that is commonly used in its crystalline form in the microelectronics field, in particular for its electrical and optical properties. The crystalline germanium-base superficial layer is advantageously a layer of germanium of single-crystal structure. This method is particularly advantageous for elements formed on a substrate on which a germanium-base layer is deposited. The element preferably consists of a germanium superficial layer formed on a substrate. The substrate can be at least partially insulating, of the "germanium-on-insulator" (GeOI) type, or be made from silicon coated with an oxide film or from silicon of the "germanium-on-silicon" (GOS) type.

The substrate can also be of any kind, either bulk or formed by several layers, for example a silicon layer and a silicon-germanium alloy layer.

The method can apply to a bulk element or to an element having a crystalline germanium-base superficial layer of any thickness and in particular less than 500 nm, preferably comprised between 10 nm and 100 nm, unlike chemical etching methods which on account of their high etching rate are rather reserved for layers having a thickness of more than 500 nm.

According to a known method, GOS wafers can be obtained by epitaxy, i.e. growth of crystals of a thin layer of germanium on a suitable substrate, for example made from silicon and/or SiGe. The GeOI wafers can for their part be obtained by condensation of a SiGe film or by transfer of layers. According to the latter technique, a germanium substrate can for example be assembled by molecular bonding on an oxidized silicon substrate and the germanium substrate then be thinned. Thinning can be performed by mechanical means or by fracturing at the level of a buried weakened area present in the germanium substrate and obtained for example by implantation of gaseous species performed before bonding, a method known under the name of Smart Cut™ method.

According to a particular embodiment, the method for revealing emergent dislocations of an element having at least one crystalline germanium-base superficial layer comprises an annealing step of the element in an atmosphere having a base that is a mixture of at least an oxidizing gas and a neutral gas. The annealing step is implemented in a furnace. The method can be carried out without any pre-treatment of the element. It can advantageously consist of a single annealing step and can be performed on full wafers, for example with diameters of 200 mm or 300 mm, or on fragments of wafers.

Oxidation by annealing of the element is selective on account of the stress field created by the dislocation and/or of the dislocation impurities segregation phenomenon. The presence of a dislocation at the surface of the germanium-base layer does in fact give rise to an imperfection close to the dislocation which enhances oxidation of the germanium atoms into germanium oxide. The rate of oxidation at the level of the dislocations is therefore faster than that of the germanium in the perfect crystal lattice. The germanium oxide thus created sublimates at a temperature of about 500° C. to 550° C. The gas used is for example oxygen for the oxidizing gas and nitrogen and/or argon for the neutral gas. The gas flow transports the germanium oxide formed at the surface of the germanium superficial layer and enhances the oxidation reaction. A part of the thickness of the germanium superficial layer is then consumed by this treatment. This etching phenomenon can be characterized by an etching rate that corresponds to the value of the thickness of the superficial layer consumed per hour of heat treatment. The method for revealing emergent dislocations is however hardly material-destructive as the etching rate remains slow compared with the chemical etching used in the prior art for revealing defects in germanium. Depressions are thereby created at the surface of the germanium layer at the level of the emergent dislocations. They appear in the form of dots visible by conventional observation techniques. The emergent dislocations thus revealed are for example directly observable by any automatic production line defect detection and counting equipment or, in simple manner, by optical or electronic microscopy. The dislocation density, i.e. the number of emergent dislocations per $cm^2$, is then able to be calculated.

The annealing step is preferably performed at an annealing temperature higher than or equal to 500° C. for a set period corresponding to the annealing time. The annealing time and temperature are to be determined according to the thickness of the superficial layer and the expected dislocation density. The greater the thickness, the longer the annealing time will be able to be, as more material will be able to be removed without degrading the quality of the residual superficial layer. The higher the expected dislocation density, the lower the annealing temperature and the shorter the annealing time will have to be, to prevent the depressions created from becoming too large and merging, thus making any significant counting impossible.

According to a preferred embodiment, the annealing temperature is comprised between 500° C. and 700° C., preferably comprised between 530° C. and 570° C. and preferably equal to 550° C. To avoid causing damage to the superficial layer or a loss of integrity of the element, the annealing temperature should not exceed a temperature of about 700° C.

A mixture of oxygen $O_2$ and at least an inert gas, for example a mixture of oxygen $O_2$ and nitrogen $N_2$, is preferably maintained in the furnace to submit the element to an oxidizing atmosphere during heat treatment. The proportion of oxygen in the mixture is comprised between 0.5% and 95%.

For the oxidizing gas, other oxidizing species can be used, for example water vapor ($H_2O$) or nitrous oxide ($N_2O$).

For example purposes, four wafers having a germanium-base superficial layer were treated by the method described above without pre-treatment and full-wafer for a better representativeness of the results. Observation of the revealed emergent dislocations was performed by means of an optical microscope (of Zeiss trademark) with a ×100 enlargement (41 μm×31 μm field size). The first and second wafers are silicon substrates covered with an epitaxially grown germanium layer, respectively GOS-(1) and GOS-(2). The third wafer is a bulk germanium wafer Ge-(1). The fourth wafer is a GeOI-(1) wafer obtained by transfer of a thin layer of germanium coming from a similar wafer to the GOS-(1) wafer onto a silicon substrate oxidized by the Smart Cut™ method.

Each of the wafers was treated under the same conditions i.e. at an annealing temperature equal to 550° C. for 1 hour under an oxygen and nitrogen gas flow with a ratio respectively of 0.7% and 99.3%. Under these conditions, the etching rate is about 20 nm/hour.

FIG. 1 represents the micrograph obtained from the first wafer GOS-(1). It reveals the presence of emergent dislocations that appear in the form of dots 1. Analysis by counting evaluates a dislocation density of $1.5*10^7$ dislocations/$cm^2$.

Figure 2:
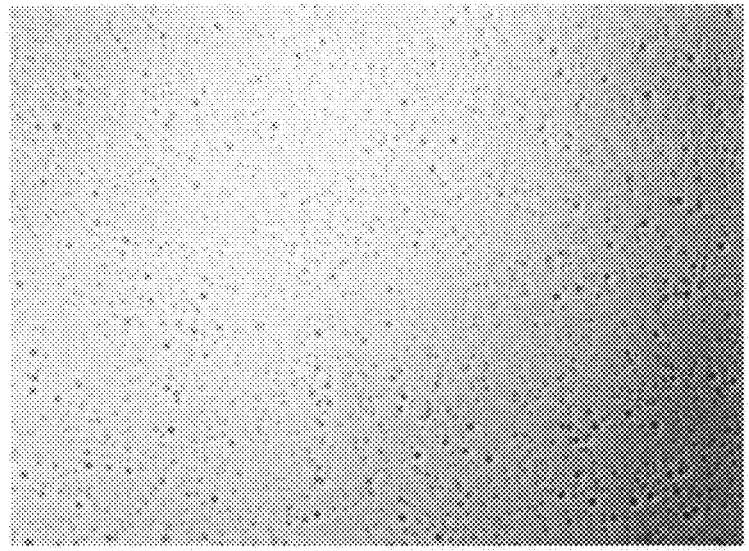
FIG. 2 represents an optical micrograph of a sample of a second GOS (2) wafer after revelation according to the method of the invention.

FIG. 2 represents the micrograph obtained from the second wafer GOS-(2). Analysis by counting enables a dislocation density of $1.2*10^8$ dislocations/$cm^2$ to be determined. It can be observed that this dislocation density is greater than that of first wafer GOS-(1).

Figure 3:
FIG. 3 represents an optical micrograph of a sample of a bulk germanium Ge (1) wafer after revelation according to the method of the invention.

As represented in FIG. 3, the micrograph obtained in optical microscopy of wafer Ge-(1) reveals a smooth superficial layer with no depressions (dots). Germanium wafer Ge-(1) has a perfect single-crystal structure at the level of its superficial layer.

Figure 4:
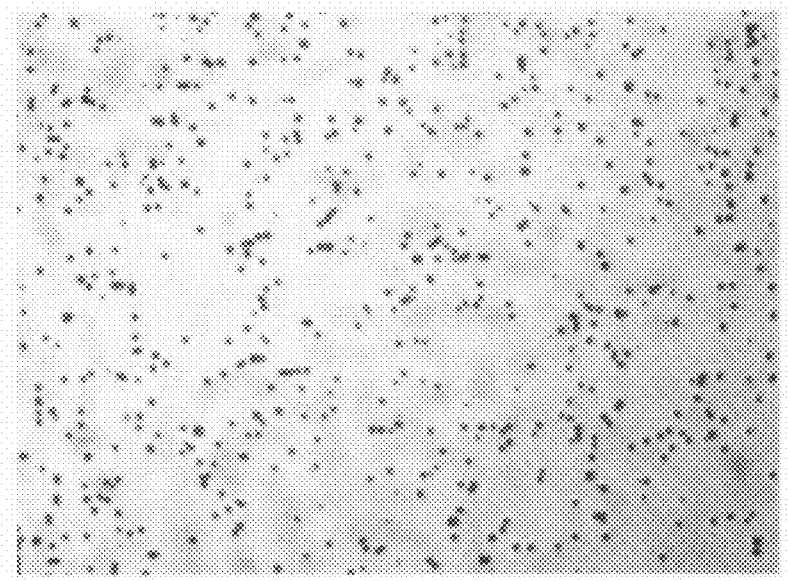
FIG. 4 represents an optical micrograph of a sample of a GeOI (1) wafer after revelation according to the method of the invention.

The micrograph obtained from fourth wafer GeOI-(1) is represented in FIG. 4. The germanium layer of GeOI-(1) has a thickness of 50 nm. The emergent dislocation density was determined by counting the observed dots. This density is $3.8*10^7$ dislocations/$cm^2$. These results are of the same order of magnitude as those observed on first wafer GOS-(1), which tends to prove that the film transfer method used did not significantly induce any additional defects in the germanium layer. This also confirms that our method for revealing emergent dislocations can be applied to very thin layers.

Figure 5:
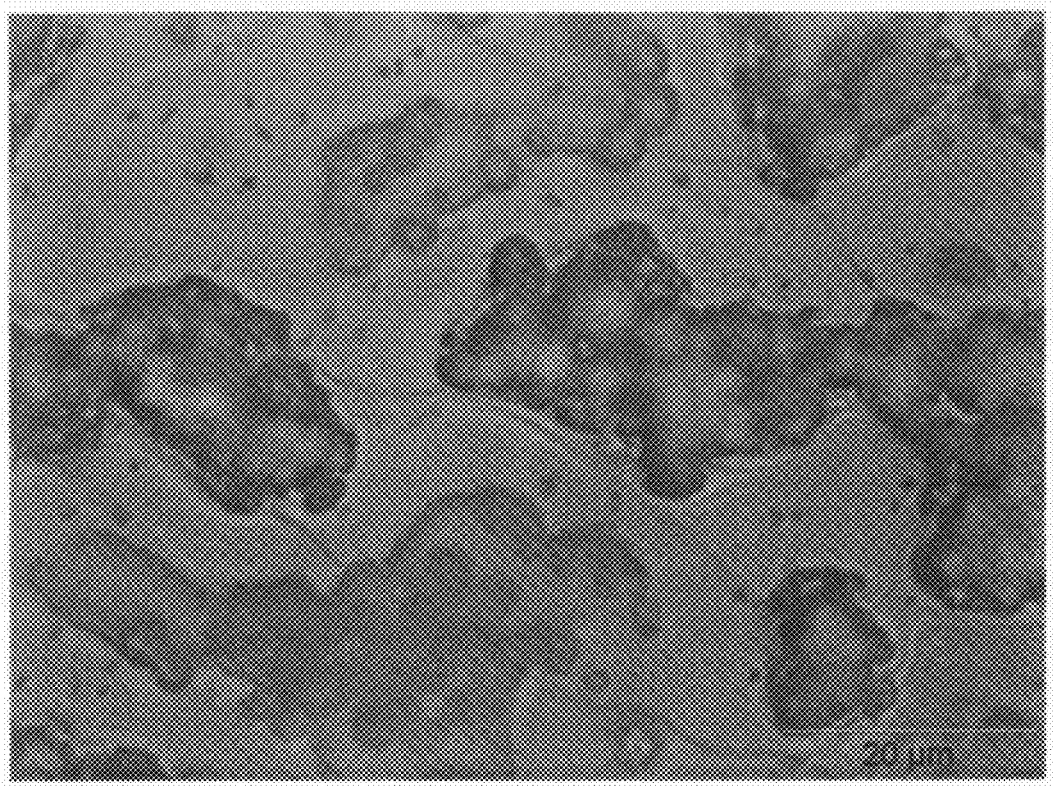
FIG. 5 represents an optical micrograph of a sample of a third GOS (3) wafer after revelation according to the method of the invention performed at an annealing temperature of 700° C.

FIG. 5 represents the optical micrograph obtained from second wafer GOS-(2) subjected to the method for revealing emergent dislocations described above but with an additional step at a temperature of 700° C. A significant deterioration of the integrity of the surface of wafer GOS-(2) can be observed, this wafer no longer being usable.

The results obtained by this method enable the elements to be sorted to select those that present the best crystalline qualities i.e. the least emergent dislocations. This method can be integrated in a production line or can for example serve the purpose of selecting an element from several elements provided by different suppliers.

According to an alternative embodiment, the method can comprise other treatment steps, for example pre-treatment to eliminate a passivation layer at the surface of the element should such a layer exist.

According to another alternative embodiment, annealing can be optimized by subjecting the element to a temperature gradient with one or more temperature plateaus.

The method described above enables emergent dislocations of a germanium-base superficial layer to be revealed under conditions that are not aggressive with an etching rate that is compatible with germanium-base thin layers, i.e. having a thickness of less than 500 nm, or even less than 50 nm. This method is therefore suitable for GeOl and GOS wafers.

Furthermore, unlike prior-art methods, the method for revealing emergent dislocations described above does not use products that are corrosive or harmful for man and the environment. It furthermore does not require specifically trained personnel as it is simple to implement, without any prior preparation of the element. This efficient industrializable method can be used for etching of both fragments and full wafer and gives representative and reproducible results.

The invention claimed is:

1. A method for detecting defects comprising:
conducting selective oxidation of germanium atoms into germanium oxide by at least an annealing treatment, said annealing treatment being performed in an atmosphere having a base that is a mixture of at least an oxidizing gas and a neutral gas;
enabling the germanium oxide created by the selective oxidation to sublimate in order to create depressions at a surface of an element; and
revealing emergent dislocations of the element having at least one crystalline germanium-base superficial layer.

2. The method according to claim 1, wherein the oxidizing gas is oxygen.

3. The method according to claim 2, wherein the proportion of oxygen in the mixture is comprised between 0.5% and 95%.

4. The method according to claim 1, wherein the oxidizing gas is chosen from water vapor and nitrous oxide.

5. The method according to claim 1, wherein the neutral gas is nitrogen and/or argon.

6. The method according to claim 1, wherein the element consists of a germanium superficial layer formed on a substrate.

7. The method according to claim 6, wherein the substrate is at least partially insulating.

8. The method according to claim 6, wherein the substrate is made from silicon coated with an oxide film.

9. The method according to claim 6, wherein the substrate is made from silicon.

10. The method according to claim 1, wherein the crystalline germanium-base superficial layer has a thickness of less than 500 nm.

11. The method according to claim 10, wherein the thickness is comprised between 10 nm and 100 nm.

12. The method according to claim 1, wherein the annealing treatment is performed at an annealing temperature comprised between 500° C. and 700° C.

13. The method according to claim 12, wherein the annealing temperature is comprised between 530° C. and 570° C.

* * * * *